United States Patent [19]
Creeth et al.

[11] Patent Number: 6,153,219
[45] Date of Patent: Nov. 28, 2000

[54] ORAL COMPOSITION

[75] Inventors: Jonathan Edward Creeth; Andrew Joiner; William John Stead, all of Bebington, United Kingdom

[73] Assignee: Unilever Home & Personal Care USA, division of Conopco, Inc., Greenwich, Conn.

[21] Appl. No.: 09/312,274

[22] Filed: May 14, 1999

[30] Foreign Application Priority Data

May 15, 1998 [GB] United Kingdom .................. 9810519
Nov. 12, 1998 [GB] United Kingdom .................. 9824876

[51] Int. Cl.[7] ............................ A61K 9/48; A61K 9/127; A61K 9/20; A61K 7/16
[52] U.S. Cl. .............................. 424/451; 424/49; 424/62; 424/450; 424/464
[58] Field of Search ................................ 424/489, 401, 424/65, 67, 49, 62, 450, 451

[56] References Cited

U.S. PATENT DOCUMENTS 5,631,013  5/1997  Bergmann et al. ..................... 424/401

Primary Examiner—Thurman K. Page
Assistant Examiner—Susan Tran
Attorney, Agent, or Firm—Milton L. Honig

[57] ABSTRACT

An oral care composition comprises capsules which comprise an encapsulated agent encapsulated by an encapsulating material stable in the presence of anionic surfactants, said encapsulated agent being capable of providing a cosmetic, sensory, protective or therapeutic benefit to the oral cavity, wherein the capsules' weight average particle size ranges from 100 to 2000 $\mu$m and wherein the capsules are capable of being gradually crushed during brushing thereby releasing the encapsulated agent gradually during brushing, the foaming capability being maintained throughout brushing.

10 Claims, No Drawings

ORAL COMPOSITION

BACKGROUND OF THE INVENTION

1. Field of the Invention

The present invention relates to an oral composition, in particular an oral composition with improved cosmetic, sensory, protective and therapeutic benefits for the oral cavity.

2. The Related Art

More particularly, it relates to an oral care composition which contains an encapsulated agent, capable of exerting a cosmetic, sensory, protective or therapeutic benefit in the oral cavity.

Dentifrice compositions comprising encapsulated materials are already known in the art. For example, JP 55 100 309 (Lion) discloses a dentifrice composition comprising microcapsules comprising silicone oil which is a foam-depressing agent. The capsules according to this invention have an average particle size ranging from 5 to 50 $\mu$m. The capsules are designed so as to be crushed and thereby release the silicone oil only after a recommended period of brushing has elapsed. In this way the anti-foam effect of the silicone oil provides a sensorial indication to the user that a suitable period of brushing has elapsed.

The disadvantages with such small microcapsules are that they are less likely to get trapped by the tip end of the toothbrush and are, therefore, less likely to be ruptured during brushing, so that the microcapsules remaining unbroken are liable to cause lowering of the sense of pleasant feeling. They may also be too small to provide any visual aesthetic effect to the consumer. Furthermore, they may get trapped in the interdental spaces.

GB 1 381 444 (Blendax-Werke) discloses a highly speckled toothpaste comprising microcapsules having a transparent shell material encapsulating a solution or suspension of colouring matter in a physiologically inert solvent. An especially preferred physiologically inert solvent is paraffin oil and the capsules have an average particle size ranging from 100 to 900 $\mu$m. The capsules described are designed to crush immediately during use, which implies that their contents, i.e. the colouring matter and the paraffin oil, are also released immediately. This causes an immediate foam depression, as paraffin oil is a known foam depressing agent.

EP-A-0 711 544 (Kao) discloses a dentifrice composition comprising capsules containing agar as a main component of a coating forming substance. The capsules have an average diameter of from 0.3 to 3 mm.

However, agar is an unstable material in the presence of anionic surfactants, e.g. alkali metal alkyl sulphate surfactants, such as sodium lauryl sulphate, which is a conventional material commonly used in dentifrice compositions, and these capsules, made from agar as coating forming material suffer from leaching in such dentifrice compositions.

SUMMARY OF THE INVENTION

We have now surprisingly found, that the inclusion in an oral care composition of capsules which comprise an encapsulated agent encapsulated by an encapsulating material which is stable in the presence of anionic surfactants, said encapsulated agent being capable of providing a cosmetic, sensory, protective or therapeutic benefit to the oral cavity, wherein the capsules' weight average particle size ranges from 100 to 2000 $\mu$m and wherein the capsules are capable of being gradually crushed during brushing thereby releasing the encapsulated agent gradually during brushing provides an oral care composition with an improved oral care benefit to the consumer. In this way, the foaming can be maintained throughout brushing with a dentifrice composition of the invention even when the capsules comprise an anti-foam substance.

Preferably the weight average particle size ranges from 600 to 1400 $\mu$m, more preferably from 700 to 1200 $\mu$m.

Typical encapsulating materials are common in the art and include but are not limited to cyclodextrin, gum arabic, gelatin, casein, albumin, fibrinogen, xanthan gum, haemoglobin, soluble collagen peptides, sodium alginate, carboxy-methyl cellulose, carrageenan, polyvinylpyrrolidone and similar natural or synthetic polymeric materials. Many suitable encapsulating materials are cross-linked. Cross-linking may be inherent in the encapsulating material or it may be achieved by a cross-linking agent, e.g. glutaraldehyde.

DETAILED DESCRIPTION

The capsules can be made by any conventional microencapsulation process, preferably by complex coacervation. The process conditions and encapsulating materials should be carefully chosen, so that capsules are obtained which are neither too hard to survive any crushing during use, nor too soft to crush already during manufacture of the oral care composition.

The encapsulating materials should be stable in the presence of anionic surfactants, e.g. sodium lauryl sulphate. Such encapsulating materials preferably include gum arabic, gelatin and mixtures and derivatives thereof.

In a most preferred embodiment the encapsulating material is a mixture of gum arabic and gelatin, preferably a 50%—50% mixture.

It is an essential feature of the invention that the capsules are broken gradually during brushing. A surprising benefit of such gradual crushing is that the effect of materials present as core ingredients may be controlled. For example, oils, particularly silicone oils, are well known for their anti-foam effect but we have found that this anti-foam effect can be overcome if the crushing of capsules containing such oils is controlled during brushing.

Typical agents to be encapsulated by an encapsulating materials according to the invention include any agent capable of exhibiting a therapeutic, sensory, protective or cosmetic effect and include antimicrobial agents, anti-caries agents, gum protection agents, flavours, colours, whitening agents and suchlike. The encapsulated agent may comprise a single ingredient or a mixture of ingredients.

These ingredients can be any of the ingredients, commonly found in oral care compositions as set out below.

The encapsulating agent preferably comprises gum protection agents, e.g. vegetable oils such as sunflower oil, rape seed oil, soybean oil and safflower oil; mono- and diglycerides; silicone oil; and hydrocarbon oil. The gum protection agent may be an agent capable of improving the permeability barrier of the gums. A complete description of agents capable of improving the permeability barrier of the gum is found in our co-pending application GB 9824875.0.

Especially preferably, the encapsulated agent comprises an oily material, and a preferred oily material is sunflower oil. Particularly preferably said oily material also contains a colouring agent and/or a proteinaceous material such as keratin.

An example of capsules with an encapsulated agent suitable for use in the present invention is microencapsulated sunflower oil with a a weight average particle size diameter of between 800 and 1000 µm.

Particle size can be measured using conventional methods, for example, standard gauge sieves and microscopy.

Typically, the encapsulated agent will comprise from 0.01 to 10%, preferably from 0.1 to 5% and more preferably from 0.1 to 2% by weight of the oral composition according to the invention.

The oral composition according to the invention comprise further ingredients which are common in the art, such as:

antimicrobial agents, e.g. Triclosan, chlorhexidine, copper-, zinc- and stannous salts such as zinc citrate, zinc sulphate, zinc glycinate, sodium zinc citrate and stannous pyrophosphate, sanguinarine extract, metronidazole, quaternary ammonium compounds, such as cetylpyridinium chloride; bis-guanides, such as chlorhexidine digluconate, hexetidine, octenidine, alexidine; and halogenated bisphenolic compounds, such as $_{2,2}1$ methylenebis-(4-chloro-6-bromophenol);

anti-inflammatory agents such as ibuprofen, flurbiprofen, aspirin, indomethacin etc.;

anti-caries agents such as sodium- and stannous fluoride, aminefluorides, sodium monofluorophosphate, sodium trimeta phosphate and casein;

plaque buffers such as urea, calcium lactate, calcium glycerophosphate and strontium polyacrylates;

vitamins such as Vitamins A, C and E;

plant extracts;

desensitising agents, e.g. potassium citrate, potassium chloride, potassium tartrate, potassium bicarbonate, potassium oxalate, potassium nitrate and strontium salts;

anti-calculus agents, e.g. alkali-metal pyrophosphates, hypophosphite-containing polymers, organic phosphonates and phosphocitrates etc.;

biomolecules, e.g. bacteriocins, antibodies, enzymes, etc.; flavours, e.g. peppermint and spearmint oils;

proteinaceous materials such as keratin and collagen preservatives;

opacifying agents;

colouring agents;

pH-adjusting agents;

sweetening agents;

pharmaceutically acceptable carriers, e.g. starch, sucrose, water or water/alcohol systems etc.;

surfactants, such as anionic, nonionic, cationic and zwitterionic or amphoteric surfactants;

particulate abrasive materials such as silicas, aluminas, calcium carbonates, dicalciumphosphates, calcium pyrophosphates, hydroxyapatites, trimetaphosphates, insoluble hexametaphosphates and so on, including agglomerated particulate abrasive materials, usually in amounts between 3 and 60% by weight of the oral care composition;

humectants such as glycerol, sorbitol, propyleneglycol, xylitol, lactitol etc.;

binders and thickeners such as sodium carboxymethylcellulose, xanthan gum, gum arabic etc. as well as synthetic polymers such as polyacrylates and carboxyvinyl polymers such as Carbopol®;

polymeric compounds which can enhance the delivery of active ingredients such as antimicrobial agents can also be included. Examples of such polymers are copolymers of polyvinylmethylether with maleic anhydride and other similar delivery enhancing polymers, e.g. those described in DE-A-3,942,643 (Colgate);

buffers and salts to buffer the pH and ionic strength of the oral care composition; and other optional ingredients that may be included are e.g. bleaching agents such as peroxy compounds e.g. potassium peroxydiphosphate, effervescing systems such as sodium bicarbonate/citric acid systems, colour change systems, and so on.

Liposomes may also be used to improve delivery or stability of active ingredients.

By the foaming capability being maintained is meant that the level of foam produced during brushing is not reduced significantly through the inclusion of the capsules, even when the capsules comprise an anti-foam agent. Preferably, the level of foaming is at least 70%, more preferably 80% and especially 90% that of an identical composition comprising no capsules.

Further, it is understood that the level of foaming changes during brushing and approaches a maximum after between 30 and 50 s. Rinsing and expectoration naturally reduce the amount of foam in the oral cavity. It is also understood that the level of foaming depends on the toothpaste's basic formulation.

The oral compositions may be in any form common in the art, e.g. toothpaste, gel, mousse, aerosol, gum, lozenge, powder, cream, etc. and may also be formulated into systems for use in dual-compartment type dispensers.

In a preferred embodiment the oral composition according to the invention is a gel.

The present invention will be further illustrated by way of example.

EXAMPLE 1

The following dentifrice formulation represents a formulation according to the invention:

|  | Mass % |
|---|---|
| Sorbitol syrup (70%) | 62.00 |
| Abrasive silica | 8.00 |
| Thickening silica | 8.00 |
| Polyethylene glycol (MW 1,500) | 4.00 |
| Sodium laurylsulphate | 1.80 |
| Flavor oil | 1.20 |
| Sodium monofluoro phosphate | 1.12 |
| Sodium saccharin | 0.20 |
| Microencapsulated Sunflower Oil | 1.00 |
| (average weight particle size 800–1000 µm) | |
| Thickener (SCMC) | 0.60 |
| Water | 12.08 |

EXAMPLE 2

Capsules of silicones (poly dimethylsiloxane (50/50 100k/$5 \times 10^{-3}$ m$^2$s$^{-1}$) encapsulated by polyvinyl pyrrolidone (PVP) were stabilised in water (20% w/w) with a thickener (a cross-linked polyvinylmethylether/maleic anhydride copolymer). The capsules had a weight average particle size of 200 µm and such capsules are available commercially from ISP.

A standard toothpaste formulation as shown in Table 1 was post-dosed with capsules to give 0.4, 0.8, 1.2 and 1.6% w/w silicone in the toothpaste.

TABLE 1

| Ingredient | % by weight |
|---|---|
| Sorbitol (70% aq) | 45.00 |
| Abrasive silica | 10.00 |
| Thickening silica | 8.00 |
| Structurant (PEG Mr 1500) | 5.00 |
| SLS | 1.50 |
| Titanium dioxide | 1.00 |
| Flavor Oil | 1.00 |
| Thickener (SCMC) | 0.90 |
| Sodium fluoride | 0.32 |
| Potassium sorbate | 0.30 |
| Sodium saccharin | 0.17 |
| Monosodium phosphate | 0.10 |
| Water | 26.71 |

The sample of toothpaste and capsule (10 g) was slurried with 30 g of a diluent (comprising 5% w/w glycerol; 0.5% SCMC; 0.01% of 39.3% solution of formalin in water; and 94.49% water) and then placed in a in vitro foam measuring device. The slurry was agitated in a way that caused gradual crushing of the capsules for 30, 60 and 120 s in total and the foam volume measured.

The results are shown in Table 2.

TABLE 2

| Time (s) | Foam volume (ml) | | | | |
|---|---|---|---|---|---|
| | 0% silicone | 0.4% | 0.8% | 1.2% | 1.6% |
| 0 | 0 | 0 | 0 | 0 | 0 |
| 30 | 24 | 22 | 20 | 20 | 28 |
| 60 | 34 | 37 | 34 | 34 | 48 |
| 90 | 55 | 58 | 50 | 54 | 62 |

It can clearly be seen that the incorporation of these capsules, even with high quantities of the silicone anti-foam agent, did not cause any loss in foam of the toothpaste upon use.

EXAMPLE 3

In-Vitro Foaming Device:

A motorised unit and associated gearing system are housed in a metal casing and provide up-and-down motion to an attached toothbrush which extends from the front of the unit. Suitable toothbrushes are those with a straight handle and of regular size.

A sample cell is constructed comprising 500 ml graduated cylinder and a supported denture fixed vertically to the inner wall of the cylinder and positioned below the toothbrush so as to ensure brushing consistency.

Reproducible brush-deformation between experiments is attained by ensuring that the sample cell is pressed tight against the wall of the motorised unit.

A typical denture is available from Detreys Diatorics and comprises a full set of wired teeth.

A typical brushing frequency used was 250 strokes/min.

EXAMPLE 4

The following in vitro analysis can also be used to measure foaming.

A sample (1 g) of toothpaste was put on a toothbrush and brushed in the oral cavity for 30 s. The foam was expectorated into a measuring cylinder and left for 2 min. Where the capsules were burst before use, simulating immediate rupture, they were passed through a 200 μm plastic mesh. The experiments for each sample were performed in triplicate and the foam heights averaged.

The capsules used were those which broke gradually during brushing.

The formulation illustrated in Example 1 was used, minus the capsules for the control; with capsules which broke gradually during brushing; and with capsules which were ruptured before brushing to simulate capsules which break immediately.

TABLE 3

| Sample | Average level of foam (mm) |
|---|---|
| No capsules | 24 |
| Capsules | 22 |
| Ruptured capsules | 16 |

The results in Table 3 clearly show that the inclusion of anti-foam agent encapsulated within capsules which break gradually during brushing does not drastically reduce the level of foaming during brushing compared with capsules which are broken immediately prior to use and have a much greater effect on foaming.

What is claimed is:

1. An oral care composition comprising capsules which comprise an encapsulated agent which is a vegetable oil selected from the group consisting of sunflower oil, rape seed oil, safflower and soybean oil, the agent being encapsulated by an encapsulating material stable in the presence of anionic surfactants which is selected from the group consisting of cyclodextrin, gum arabic, gelatin, casein, albumin, fibrinogen, xanthan gum, haemoglobin, soluble collagen peptides, sodium alginate, carboxy-methyl cellulose, carrageenan and polyvinylpyrrolidone, said encapsulated agent being capable of providing a cosmetic, sensory, protective or therapeutic benefit to the oral cavity, wherein the capsules have a weight average particle size ranging from 100 to 2000 μm and wherein the capsules are capable of being gradually crushed during brushing thereby releasing the encapsulated agent gradually during brushing, the foaming capability being maintained throughout brushing.

2. A composition according to claim 1, wherein the composition is a gel.

3. A composition according to claim 1 additionally comprising an anionic surfactant.

4. A composition according to claim 3, wherein the anionic surfactant is sodium lauryl sulphate.

5. A composition according to claim 1, wherein the encapulated agent weight average particle size ranges from 600 to 1400 μm.

6. A composition according to claim 1, wherein the weight average particle size ranges from 700 to 1200 μm.

7. A composition according to claim 1, wherein the encapsulating material is selected from the group consisting of gum arabic, gelatin and mixtures thereof.

8. A composition according to claim 7, wherein the encapsulating material comprises a 50%/50% mixture of gum arabic and gelatin.

9. A composition according to claim 1, comprising 0.01–10% of capsules.

10. A composition according to claim 1, wherein the encapsulated agent is a high oleate sunflower oil.

* * * * *